US006291496B1

(12) United States Patent
Dannenberg et al.

(10) Patent No.: US 6,291,496 B1
(45) Date of Patent: Sep. 18, 2001

(54) TREATING CANCERS ASSOCIATED WITH OVEREXPRESSION OF CLASS I FAMILY OF RECEPTOR TYROSINE KINASES

(76) Inventors: Andrew J. Dannenberg, 7 Gracie Sq., Apt. 14A, New York, NY (US) 10028; Kotha Subbaramaiah, 43-23 Colden St., Apt. 17K, Flushing, NY (US) 11355

( * ) Notice: Subject to any disclaimer, the term of this patent is extended or adjusted under 35 U.S.C. 154(b) by 0 days.

(21) Appl. No.: 09/472,179

(22) Filed: Dec. 27, 1999

(51) Int. Cl.$^7$ .......................... A01N 43/76; A61K 31/42; A61K 39/395; G01N 33/574; C07D 263/62
(52) U.S. Cl. ...................... 514/376; 435/7.23; 424/130.1; 424/138.1; 424/143.1; 424/155.1; 424/156.1; 548/220
(58) Field of Search ................. 424/130.1, 138.1, 424/143.1, 156.1, 155.1; 514/376; 548/270; 435/7.23

(56) References Cited

U.S. PATENT DOCUMENTS

| | | | |
|---|---|---|---|
| 4,980,160 | 12/1990 | Goldberg et al. | 424/85.1 |
| 5,081,105 | 1/1992 | Bistrian | 514/2 |
| 5,639,738 | 6/1997 | Falk et al. | 514/54 |
| 5,766,571 | 6/1998 | Ceriani et al. | 424/1.49 |
| 5,766,920 | 6/1998 | Babbitt et al. | 435/375 |
| 5,776,891 | 7/1998 | Coon et al. | 514/10 |
| 5,776,913 | 7/1998 | Ogilvie et al. | 514/57 |
| 5,814,647 | 9/1998 | Urban et al. | 514/369 |
| 5,861,274 | 1/1999 | Evans et al. | 435/69.1 |
| 5,869,524 | 2/1999 | Failli | 514/473 |
| 5,874,235 | 2/1999 | Chan et al. | 435/18 |
| 5,902,726 | 5/1999 | Kliewer et al. | 435/7.1 |
| 5,914,322 | 6/1999 | Falk et al. | 514/54 |
| 5,925,657 | 7/1999 | Seed et al. | 514/369 |
| 5,939,442 | 8/1999 | Evans et al. | 514/357 |

OTHER PUBLICATIONS

Physician's Desk Reference, 2001, Medical Economics Co., pp. 1055, 1056, 1062.*
Beers, M.H. et al., The Merck manual of diagnosis and therapy. 1999, 17th ed. Merck Research Laboratories, pp. 1980–1982.*
Gusterson, B.A. et al., J. Clinical Oncology, 1992, vol. 10, No. 7, pp. 1049–1056.*
Yu et al., BioEssays, 2000, vol. 22, pp. 672–680.*
Yu, D. et al., Oncogene, 1998, vol. 16, pp. 2087–2094.*
Alfred, D.C. et al., J. Clinical Oncology, 1992, vol. 10, No. 4, 599–605.*
Elstner et al., Proc. Nat. Acad. Sci. USA. vol. 95, pp 8806–8811, Jul., 1998.*
Colbern et al., J. Inorg. Biochem. vol. 77, pp. 117–120, 1999.*
Read et al., Cancer Res., vol. 50, pp. 3947–3951, 1990.*
Beckhardt, R. N., et al., Arch Otolaryngol Head Neck Surg. 121, 1265–1270 (11/95).
Bue, P., et al., Int. J. Cancer 76, 189–193 (1998).

Hudson, L. G., et al., J. Biol. Chem. 265(8), 4389–4393 (Mar. 15, 1990).
Hudson, L. G., et al., Cell 62, 1165–1175 (Sep. 21, 1990).
Nichols, J. S., et al., Analytical Biochemistry 257, 112–119 (1998).
P\S\L Consulting Group, Doctor's Guide, E–mail Edition, publication dated May 20, 1997, titled "New Cancer Treatment Shows Encouraging Results" —4 pages.
Ciardiello, F., et al., J. Nat'l Cancer Inst. 90(14), 1087–1094 (Jul. 15, 1998).
Cobb, J. E., et al., J. Med. Chem. 41, 5055–5068 (1998).
Ilekis, J. V., et al., Gynecologic Oncology 66, 250–254 (1997).
ImClone Press Release, Dec. 2, 1999, titled "ImCone and Merck KGaA Initiate First International Phase III Trial Center of C225".
Pfeiffer, D., et al., Int. J. Cancer (Pred. Oncol.) 79, 49–55 (1998).
Pierce, J. H., et al., Oncogene 6, 1189–1194 (1991).
Collins, J. L., et al., J. Med. Chem. 41(25), 5037–5054 (1998).
Dittadi, R., et al., Br. J. Cancer 64(4), 741–744, "Epidermal growth factor receptor in lung malignancies. Comparison between cancer and normal tissue" (1991).
ImClone Press Release, Dec. 7, 1999, titled "ImClone Initiates Phase II Clinical Trial of C225 in Combination with Gemcitabine in Patients with Pancreatic Carcinoma".
Reese, D. M., Stem Cells 15, 1–8 (1997).
Ross, J. S., et al., Human Pathology 28(7), 827–833 (7/97).
Divgi, C. R., et al., J. Nat'l Cancer Inst. 81(21), 1616–1625 (Nov. 1, 1989).
Elstner, G., et al., Proc. Nat'l Acad. Sci. USA 95(15), 8806–8811 (Jul. 21, 1995)—MEDLINE Abstract.
ImClone Systems Incorporated web page updated Nov. 12, 1999, headed "Clinical Trials—Cetuximab".
ImClone Systems Incorporated web pages updated Nov. 12, 1999, headed "Clinical Trials," "Current Clinical Trials," "Planned Clinical Trials".
Sainsbury, J. R., et al., The Lancet, 1398–1402 (Jun. 20, 1987).

(List continued on next page.)

Primary Examiner—Yvonne Eyler
Assistant Examiner—J. Andres

(57) ABSTRACT

Cancer associated with overexpression of class I family of receptor tyrosine kinases, e.g., with overexpresssion of HER-2/neu or overexpression of epidermal growth factor receptor, are treated with strongly binding PPARγ ligands.

28 Claims, 2 Drawing Sheets

OTHER PUBLICATIONS

Slovin, S. F., et al., www.asco.org/prof/me/html/abstracts/genc/m, 1997 Abstracts #108.

Falcy, J., et al., www.asco.org/prof/me/html/abstracts/genc/m, 1997 Abstract #164.

Freeman, M.R., et al., Cancer Research, Nov. 15, 1989, 6221–6225.

Kapitanovic, S., et al., Gastroenterology 112, 1103–1113 (1997).

Kelloff, G. J., et al., Cancer Epidemiology, Biomarkers and Prevention 5, 657–666 (8/96).

Smith, K., et al., Cancer Research 49, 5810–5815 (Nov. 1, 1989).

Suh, N., et al., Cancer Research 39, 5671–5673 (Nov. 15, 1999).

Goldenberg, A., et al., J. Nat'l Cancer Inst. 8(21), 1616–1625 (11/89).

Goldstein, N. I., et al., Clinical Caner Research, vol. 1, 1311–1318 (11/95).

Kilgore, M. W., et al., Mol. Cell Endocrinol 129(2), 229–235 (May 15, 1997)—MEDLINE Abstract.

Kim, J. W., et al., Gynecologic Oncology, 60, 283–287 (1996).

Stampfer, M. R., et al., Proc. Nat'l Acad. Sci. USA 82, 2394–2398 (4/85).

Tsugawa, K., et al., Oncology 55, 575–481 (1998).

Henke, B. R., et al., J. Med. Chem. 41, 5020–5036 (1998).

Korc, M., Surgical Oncology Clinics of North America 7(1), 25–41 (1/98).

McNeil, C., Journal of the National Cancer Institute 90(12), 882–883 (Jun. 17, 1998).

U, H. S., et al., J. Neurosurg. 82, 841–846 (1995).

Zhai, Y.–F., et al., Cancer Res. 53, 2272–2278 (May 15, 1993).

* cited by examiner

TREATING CANCERS ASSOCIATED WITH OVEREXPRESSION OF CLASS I FAMILY OF RECEPTOR TYROSINE KINASES

TECHNICAL FIELD

This invention is directed to treatment of class I family of receptor tyrosine kinases overexpressing cancers.

BACKGROUND OF THE INVENTION

The class I family of receptor tyrosine kinases is described in Reese, M. D., et al, Stem Cells, 15, pages 1–8 (1997), the whole of which is incorporated herein by reference. Members of this family include HER-2/neu, HER-3, HER-4 and epidermal growth factor receptor (EGFR) and are single-chain membrane spanning proteins which have significant homology to one another including about 80% amino acid identity in the tyrosine kinase domain.

HER-2/neu (erbB-2) gene product is a 185-kDA transmembrane receptor tyrosine kinase that is described in some detail in said Reese et al publication and overexpression thereof has been associated with tumor growth in several kinds of cancer.

Recently enormous attention has been given to the importance of HER-2/neu in breast cancer. HER-2/neu is overexpressed in 20–30% of breast cancers and the increased expression has been associated with poor patient prognosis. This discovery has led to the development of HERCEPTIN®, an antibody to HER-2/neu, which in tests has been found to lengthen remission time in metastatic breast cancer. HER-2/neu is a cell-surface receptor that transmits growth signals to the cell nucleus. HERCEPTIN® appears to block these signals thereby apparently inhibiting proliferation of cells mediated by HER-2/neu in HER-2/neu positive breast cancer.

Epidermal growth factor receptor (EGFR) is a 170 kDA glycoprotein. It is a prototypical transmembrane protein that consists of an extracellular ligand-binding domain, a transmembrane domain, and an intracellular domain that possesses intrinsic tyrosine kinase activity. After ligand binding, EGFR undergoes dimerization which is essential for activation of its enzymatic kinase activity. EGFR is thus autophosphorylated and transphosphorylated on tyrosine residues, and the phosphorylated residues become the sites of association of effector proteins. Overexpressed EGFR is intimately involved in modulating the epidermal growth factor growth signal and is considered as likely to confer a growth advantage. This conclusion is supported by the observation that tumor growth in nude mice is inhibited by treatment with anti-EGFR antibodies and tumorigenicity in nude mice is inhibited through blockage of the tyrosine kinase activity of the receptor. EGFR has been found to be overexpressed in many malignancies. Anti-EGFR antibodies are being tested as therapy for malignancies overexpressing EGFR.

Peroxisome proliferator-activated receptor γ (PPARγ) ligands are currently being used for treatment of type 2 diabetes. Moreover, MCF-7 and T47D human breast cancer cells have been found to contain a functional PPAR response; see Kilgour, M. W., et al, Mol. Cell Endocrinol, 129:2, 229–235 (May 5, 1997). Furthermore, a ligand for PPAR-γ has been found to inhibit rat mammary carcinogenesis in NMU injected female Sprague Dawley rats; see Suh, N., et al, Cancer Research 59, 5671–5673 (Nov. 15, 1999). However, administration of PPARγ ligands has not heretofore been associated with decreasing levels of HER-2/neu or EGFR or of having therapeutic benefit based thereon in treating cancers associated with overexpression of these including the subset of breast cancer associated with overexpression of HER-2/neu.

SUMMARY OF THE INVENTION

It has been discovered that PPARγ ligands cause dose dependent decreases in levels of HER-2/neu and EGFR in cultured human mammary epithelial cells. This led to the conception that cancers associated with overexpression of one or more class I family of receptor tyrosine kinases would be effectively treated with such PPARγ ligands.

The broad invention herein is directed at a method for treating cancer associated with overexpression of at least one member of the class I family of receptor tyrosine kinases in a patient affected with this condition, comprising administering to said patient a therapeutically effective amount of a ligand of peroxisome proliferator-activated receptor gamma (PPARγ) which has a $pK_i$ of at least 4.0, preferably of at least 5.0, in a binding assay using the human PPARγ binding domain.

In the case where the member of the class I family of receptor tyrosine kinases is HER-2/neu, the PPARγ ligand can be administered as the only therapy or in a combination regimen with a therapeutically effective amount of HERCEPTIN®, a HER-2/neu antibody available from Genentech, and/or conventional therapy for the kind of cancer being treated.

In the case where the member of the class I family of receptor tyrosine kinases is EGFR, the PPARγ ligand can be administered as the only therapy or in a combination therapy with a therapeutically effective amount of anti-epidermal growth factor receptor antibody, e.g., Cetuximab®, a chimeric antibody to epidermal growth factor receptor, supplied by ImClone Systems Incorporated, and/or conventional therapy for the kind of cancer being treated.

In a narrower embodiment, the invention is directed at a method of treating breast cancer associated with overexpression of HER-2/neu and/or EGFR in a patient affected with this condition, comprising administering to said patient a therapeutically effective amount of a PPARγ ligand which has a $pK_i$ of at least 4.0, preferably of at least 5.0, in a binding assay using the human PPARγ binding domain. The PPARγ ligand can be administered for or as part of adjuvant therapy for HER-2/neu positive and or EGFR positive breast cancer or for treatment of or as part treatment of HER-2/neu positive and/or EGFR positive breast cancer that has metastasized. The PPARγ ligand is preferably administered in combination therapy with HERCEPTIN® for HER-2/neu positive breast cancer and with Cetuximab® for EGFR-positive breast cancer and preferably also is administered in combination regimen with standard chemotherapy and/or endocrine therapy and/or radiation treatment.

The terms "cancer associated with overexpression of at least one member of the class I family of receptor tyrosine kinases"/"cancer associated with overexpression of HER-2/neu"/ "cancer associated with overexpression of EGFR" are used to mean the cancerous tissue contains more of the member of the class I family of receptor tyrosine kinases than non-cancerous tissue from the same portion of the body.

The term "HER-2/neu positive breast cancer" is used to refer to cancer associated with overexpression of HER-2/neu.

The term "EGFR positive breast cancer" is used to refer to cancer associated with overexpression of EGFR.

The terms "peroxisome proliferator-activated receptor gamma ligand," "ligand of peroxisome proliferator-activated receptor gamma," and "PPARγ ligand" are used to mean agent that binds to the human PPARγ binding domain as determined in a scintillation proximity assay with $K_i$ being determined in said assay as described below. The human PPARγ gene structure has been found to include two isoforms of PPARγ, denoted PPARγ1 and PPARγ2, with a common ligand binding domain.

DETAILED DESCRIPTION

Figure 1:
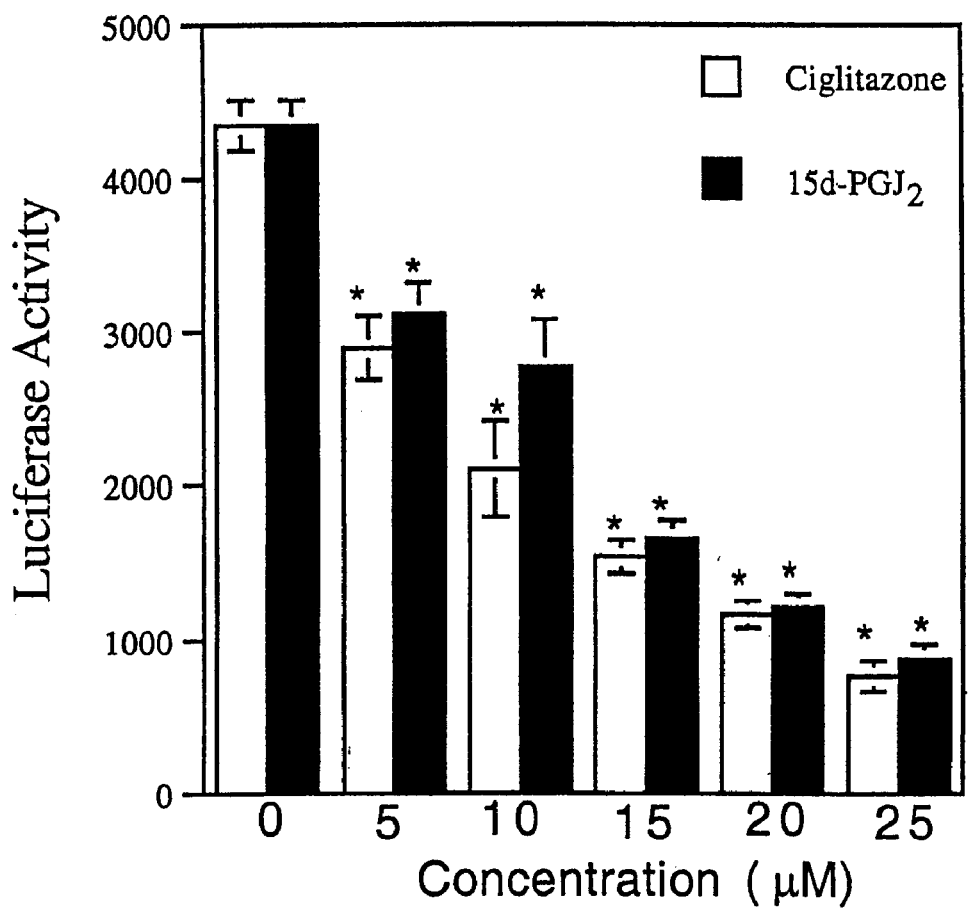
FIG. 1 is a graph of concentration of ciglitazone and 15-deoxy-Δ12, 14-prostaglandin $J_2$ (15-d-$PGJ_2$ or 15d-$PGJ_2$) versus luciferase activity and shows results of Background Example 1.

The cancers associated with overexpression of HER-2/neu include all those cancers where overexpression of HER-2/neu is found in cancerous tissue and comprise breast cancers, ovarian cancers, gastric cancers, endometrial cancers, salivary cancers, pancreatic cancers, prostate cancers, colorectal cancers and non-small-cell lung cancers.

Assays for HER-2/neu overexpression have been developed or are under development. These include the Vysis Path Vysion HER2 DNA Probe Kit developed by Vysis Inc., Downer's Grove, Ill. which is based on fluorescent in situ hybridization and a diagnostic kit being developed by DAKO A/S of Glostrup, Denmark which is directed to detecting antibodies to the HER-2/neu protein based on immunohistochemistry.

The cancers associated with overexpression of EGFR include all those cancers where overexpression of EGFR is found in cancerous tissues and comprise gliomas, hepatocellular carcinomas, pancreatic cancers and cancers of the bladder, breast, cervix, colorectum, esophagus, head and neck, lung, kidney, and prostate.

Assays for EGFR overexpression are described in Smith, K, et al, Cancer Research 49, 5810–5819 (Nov. 1, 1989); Sainsbury, J. R. C., et al, The Lancet, Jun. 20, 1987, 1398–1402; Ilekis, J. V., et al, Gynecologic Oncology 66, 250–254 (1997); Kim, J. W., et al, Gynecologic Oncology 60, 283–287 (1996); Pfeiffer, D., et al, Int. J. Cancer (Pred. Oncol.) 79, 49–55 (1998); Bue, P., et al, Int. J. Cancer 76, 189–193 (1998); and U, Hoi Sang, et al J. Neurosurg 82, 841–846 (1995), all of which are incorporated herein by reference.

We turn now to the PPARγ ligands which have a $pK_i$ of at least 4.0 in binding assay using human PPARγ binding domain. These PPARγ ligands very preferably have a $pK_i$ greater than 8.25 in said assay. Compounds have been indicated to have a $pK_i$ in said assay as high as 9.1–9.2 and compounds with a $pK_i$ in said assay with a $pK_i$ of 10.0 or higher would be expected to be developed. The assay is a scintillation proximity assay and is described in Henke, B. R, et al, J. Med. Chem, 41, 5020–5036 (1998) as follows: "The PPAR ligand binding domain (LBD) was expressed in *Escherichia coli* as polyHis-tagged fusion proteins and purified. The LBD was then labeled with biotin and immobilized on streptavidin-modified scintillation proximity beads. The beads were then incubated with a constant amount of the appropriate radioligand ([$^3$H]BRL 49653 for PPARγ) and variable concentrations of test compounds, and after equilibration the radioactivity bound to the beads was measured by a scintillation counter. The amount of nonspecific binding, as assessed by control wells containing 50 μM of the corresponding unlabeled ligand, was subtracted from each data point. For each compound tested, plots of ligand concentration versus CPM of radioligand bound were constructed and apparent $K_i$ values were estimated from nonlinear least-squares fit of the data assuming simple competitive binding." BRL49653 is described in Collins, J. L., et al, J. Med. Chem. 41, No. 25, 5037–5054 (1998) as being rosiglitazone. Details of the assay are described in Nichols, J. S., "Development of a Scintillation Proxmity Assay for Peroxisome Proliferator-Activated Receptor γ Ligand Binding Domain," Analytical Biochemistry 257, 112–119 (1998), the whole of which is incorporated herein by reference.

Compounds meeting the $pK_i$ include thiazolidinediones including ciglitazone (reported to have a $pK_i$ of 5.51±0.09), pioglitazone (reported to have a $pK_i$ of 5.91±9,92), troglitazone (reported to have a $pK_i$ 6.52±0.06), and rosiglitazone (reported to have a $pK_i$ of 7.33±0.02); see Table 3 at page 5026 of Henke, B. R, J. Med. Chem 41, 5020–5036 (1998).

Another class of compounds meeting the $pK_i$ are the compounds denoted N-(2-benzoylphenyl)L-tyrosine derivatives which have a $pK_i$ of at least 4.0. Compounds in this class and their synthesis are described in Henke, B. R, et al, J. Med. Chem. 41, 5020–5036 (1998), hereinafter Henke et al; Collins, J. L., et al, J. Med. Chem. 41, 5037–5054 (1998), hereinafter Collins et al; and Cobb, J. E., J. Med. Chem. 41, 5055–5068 (1998), hereinafter Cobb et al. The whole of Henke et al, Collins et al, and Cobb et al are incorporated herein by reference.

A preferred N-(2-benzoylphenyl)-L-tyrosine derivative has the structure

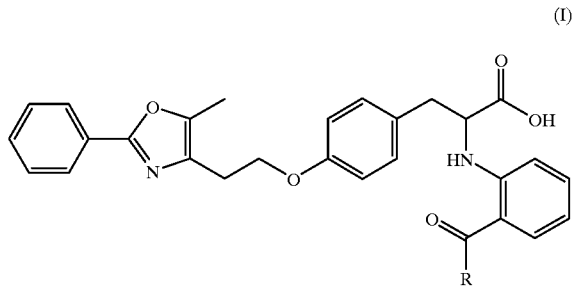

(I)

where R is OMe and is compound #63 in Cobb et al and its synthesis is described in Cobb et al. This compound is described as GW7845 in Suh, N., et al, Cancer Research 59, 5671–5673 (Nov. 15, 1999) (Nov. 15, 1999), cited above. This compound was determined to have a solubility of 0.300 mg/ml in pH 7.4 buffer. The chemical nomenclature for this compound is (S)-2-(1-carboxy-2-{4-[2-(5-methyl-2-phenyloxazol-4-yl)ethoxy]phenyl}ethylamino)benzoic acid methyl ester. This compound is reported to have a p$K_i$ of 8.43±0.02 in a binding assay the same as that defining the PPARγ ligands herein.

Another N-(2-benzoylphenyl)-L-tyrosine derivative has the structure (II)

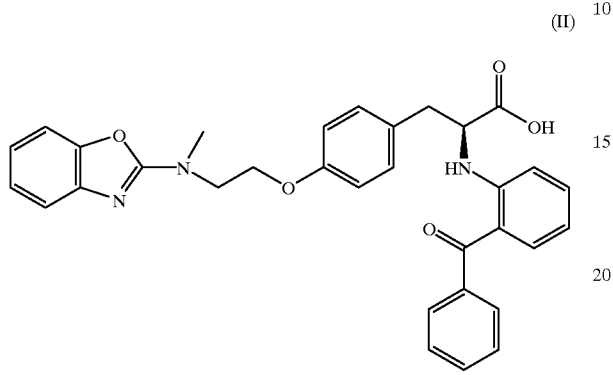

This compound is referred to as (1) in Cobb et al and (19) in Henke et al, cited above, and its method of synthesis is described in Henke et al. The chemical nomenclature for this compound is 3-{4-[2-benzoxazol-2-ylmethylamino)ethoxy](phenyl}-(2S)-((2-benzoylphenyl)amino)propionic acid. This compound is reported in Cobb et al and Henke et al as having a p$K_i$ of 8.83±0.05 in a binding assay the same as that defining the, PPARγ ligands herein.

Another N-(2-benzoylphenyl)tyrosine derivative has the structure (III)

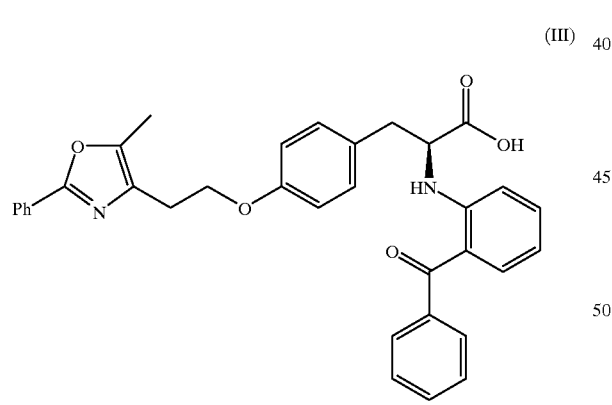

This compound is referred to as (2) in Cobb et al and (20) in Henke et al, cited above, and its method of synthesis is described in Henke et al. The chemical nomenclature for this compound is (2S)-((2-benzoylphenyl)amino)-3-{4-[2-(5-methyl-2-phenyloxazol-4-yl) ethoxy]phenyl}propionic acid. This compound is reported in Cobb et al and Henke et al as having a p$K_i$ of 8.94±0.13 in a binding assay the same as that defining the PPARγ ligands here.

Still another N-(2-penzoylphenyl)-L-tyrosine derivative has the structure (IV)

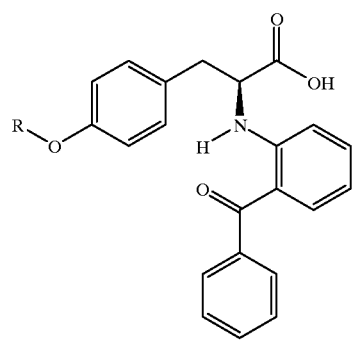

where R is

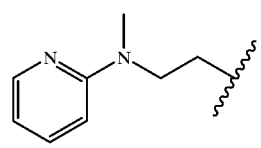

This compound is referred to as (18) in Henke et al and its method of synthesis is described in Henke et al. The chemical nomenclature for this compound is (2S)-((2-benzoylphenyl)amino)-3-{4-[2-(methylpyridin-2-ylamino)ethoxy]phenyl}propionic acid. This compound is reported in Henke et al to have a p$K_i$ of 8.35±0.02 in a binding assay the same as that defining the PPARγ ligands here.

Another N-(2-benzoylphenyl)-L-tyrosine derivative has the structure (V)

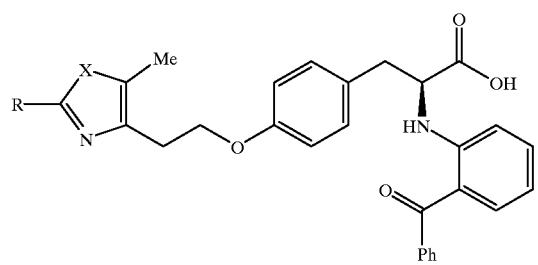

where X is O and R is

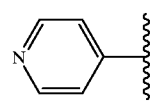

This compound is referred to as (16) in Collins et al and its method of synthesis is described in Collins et al. The chemical nomenclature for this compound is 2(S)-((2-benzoylphenyl)amino)-3-{4-[2-(5-methyl-2-pyridin-4-yloxazol-4-yl)ethoxy]phenyl}propionic acid. This compound is reported in Collins et al as having a p$K_i$ of 8.85±0.14 in a binding assay the same as that defining the PPARγ ligands herein.

Another N-(2-benzoylphenyl)-L-tyrosine derivative has the structure (V) where X is S and R is

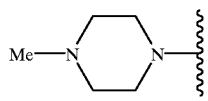

This compound is referred to as (24) in Collins et al and the method of its synthesis is described in Collins et al. The chemical nomenclature for this compound is 2(S)-((2-benzoylphenyl)amino)-3-(4-{2-[5-methyl-2-(4-methylpiperazin-1-yl)thiazol-4-yl]ethoxy}phenyl)-propionic acid. This compound is reported in Collins et al as having a $pK_i$ of 8.66±0.06 in a binding assay the same as that defining the PPARγ ligands herein.

Other N-(2-benzoylphenyl)-L-tyrosine derivatives have the structure (I) where R is ethoxy, propoxy and isopropoxy. These compounds are respectively denoted #64, #65 and #66 in Cobb et al and the synthesis of #64 is described in Cobb et al. These compounds have the same nomenclature as for #63 described above except that they are respectively the ethyl ester, the propyl ester and the isopropyl ester. These compounds are reported in Cobb et al to have $pK_i$s respectively of 8.52±0.03, 8.62±0.03 and 9.01±0.00 in a binding assay the same as that defining the PPARγ ligands herein.

Still other N-(2-benzoylphenyl)-L-tyrosine derivatives with $pK_i$ s reported to be greater than 8.25 are compounds 4, 5, 6, 7, 8, 9, 11, 12, 13, 14, 15, 17, 20, 22, 25 and 26 in Collins et al and compounds 23, 24, 26, 27, 28, 29, 30, 39, 40, 41, 45, 55, 56, 58 and 59 in Cobb et al.

Another compound meeting the $pK_i$ is 15-d-PGJ$_2$ referred to above.

The dosage of PPARγ ligand for the method of the broad embodiment is a therapeutically effective amount, i.e., a cancer cell growth inhibiting amount. In general, the dosage ranges from 0.1 μg/kg to 1,000 mg/kg per day. The dosages for any particular agent will vary within said range. For the thiozolidinediones, the dosage preferably ranges from 0.1 to 100 mg/kg, per day. For the N-(2-benzoylphenyl)-L-tyrosine derivatives, the dosage preferably ranges from 0.01 to 10 mg/kg, per day. For 15-d-PGJ$_2$, the dosage preferably ranges from 0.1 to 100 μg/kg, per day. The route of administration is preferably systemic, e.g., oral or parenteral, e.g., intravenous.

We turn now to the embodiment directed at a method of treating breast cancer associated with the overexpression of HER-2/neu and/or EGFR in a patient affected with this condition, comprising administering to said patient a therapeutically effective amount of PPARγ ligand which has a $pK_i$ of at least 4.0 in binding assay using PPARγ binding domain.

Primary treatment in the case of those determined to have breast cancer is mastectomy or breast conserving surgery (lumpectomy, tylectomy, wide excision, partial mastectomy, or quadrantectomy). Radiation therapy may be given.

Adjuvant systemic therapy is begun soon after primary therapy to delay recurrence and/or to prolong survival.

Breast cancer may metastasize to almost any organ in the body. Those most commonly involved organs include the lung, liver, bone, lymph nodes, and skin. Breast cancer also may metastasize to the central nervous system.

As indicated above, the invention herein is applicable to adjuvant therapy for HER-2/neu positive breast cancer and/or EGFR positive breast cancer and to treating HER-2/neu positive breast cancer and/or EGFR positive breast cancer that has metastasized.

The presence of HER-2/neu positive breast cancer is diagnosed by assays for HER-2/neu overexpression, e.g., as described above, carried out on breast cancer tissue.

The presence of EGFR positive breast cancer is diagnosed by assays for EGFR overexpression, e.g., as described above, carried out on breast cancer tissue.

The PPARγ ligands for use in treating HER-2/neu and/or EGFR positive breast cancer are the same as those described generally above in connection with treating cancers associated with the overexpression of HER-2/neu and/or EGFR, and for adjuvant therapy for breast cancer, a therapeutically effective amount is a breast cancer cell growth inhibiting amount, and for treating breast cancer that has metastasized, a therapeutically effective amount is a metastatic cell growth inhibiting amount. For adjuvant therapy, administration is continued for two to five years. In the case of metastasized breast cancer, treatment is preferably continued until no further response is seen.

As indicated above, the PPARγ ligands may be used as the sole treatment agent in treating HER-2/neu and/or EGFR positive breast cancer. However, for HER-2/neu positive breast cancer, the PPARγ ligands are preferably utilized in combination regimen, for example, with HERCEPTIN®. When HERCEPTIN® is used as part of the therapy for breast cancer or other cancers associated with the overexpression of HER-2/neu, a loading dose of 4 mg/kg IV is given followed by a weekly maintenance dose of 2 mg/kg IV. For EGFR positive breast cancer, the PPARγ ligands are preferably utilized in combination regimen, for example, with anti-EGFR antibodies. An anti-EGFR antibody being used in human research is called CETUXIMAB® and is also known as C225 and is anti-EGFR antibody 225 (a highly specific murine monoclonal antibody that binds specifically to human EGFR with an affinity equal to its ligand, competes with the ligand for binding and blocks activation of the receptor tyrosine kinase) chimerized to human IgG1 constant region. The biochemical and biological characteristics of the chimerized monoclonal antibody C225 are described in Goldstein, N. I., et al., Clinical Cancer Research, Vol. 1, 1311–1318 (11/85) which is incorporated herein by reference. When anti-EGFR antibodies are given as part of the therapy for breast cancer or other cancers associated with overexpression of EGFR, the dosage for CETUXIMAB® can be, for example, 100 to 400 mg/m$^2$ and the route of administration can be, for example, intravenous. The PPARγ ligands are, preferably administered in combination therapy with standard therapy. One kind of standard adjuvant therapy is adjuvant tamoxifen therapy given for two to five years. Adjuvant chemotherapy is given routinely to all pre-menopausal, node-positive patients. Adjuvant tamoxifen therapy is given routinely to post-menopausal women who are node positive and have estrogen-receptor positive tumors. Standard therapies for patients with metastatic disease include endocrine therapy or chemotherapy or in some cases radiation therapy to palliate symptoms. Chemotherapies used for treating metastatic disease include paclitaxel (TAXOL®) or combination regimen of cyclophosphamide (CYTOXAN®) and doxorubicin (ADRIAMYCIN®). Treatments herein for metastatic HER-2/neu positive breast cancer include a therapeutically effective mount of PPARγ ligand used in combination regimen with HERCEPTIN® plus a conventional dosage of paclitaxel or used in a combination therapy with HERCEPTIN® plus a conventional dosage of cyclophosphamide and doxorubicin. Treatments herein for metastatic EGFR positive breast cancer include a therapeutically effective amount of PPARγ ligand used in a combination regimen with anti-EGFR antibody plus a conventional dosage of paclitaxel or used in a combination therapy with anti-EGFR antibody plus a conventional dosage of cyclophosphamide and doxorubicin.

The invention is illustrated by the following examples which are supported by the following background examples.

BACKGROUND EXAMPLE 1

Showing that PPARγ Ligands Cause Decrease in Amount of HER-2/neu in Human Mammary Epithelial Cells The cells used were 184B5/HER and BT474 cells.

The 184B5/HER cell line was obtained from a collaborator and was derived by stably transfecting 184B5 cells with a mutationally activated HER-2/neu oncogene; these cells form rapidly growing tumors when injected into athymic nude mice. The 184B5/HER cell line is described in Pierce, J. H., et al., Oncogene 6, 1189–1194 (1991). The BT-474 cell line is a human breast cancer adenocarcinoma cell line which overexpresses HER-2/neu, and was obtained from the American Type Culture Collection (Manassas, Va.) and bears accession number ATCC HBT-20.

184B5/HER cells were maintained in MEM-KBM mixed in a ratio of 1:1 (basal medium) containing epidermal growth factor (10 ng/ml), hydrocortisone (0.5 μg/ml), transferrin (10 μg/ml), gentamicin (5 μg/ml) and insulin (10 μg/ml) (growth medium). 185B5/HER cells were grown to 60% confluence, trypsinized with 0.05% trypsin-2 mM ethylenediaminotetraacetic acid, and plated for experimental use. BT-474 cells were maintained in DMEM/F-12 medium containing 10% fetal calf serum BT-474 cells were grown to 60% confluence and trypsinized with 0.05% trypsin-2 mM ethylenediaminetetraacetic acid and plated for experimental use.

184B5/HER cells were treated with vehicle (0.01% dimethylsulfoxide), 25 μM ciglitazone (Biomol, Plymouth Meeting, Pennsylvania) or 20 μM 15-d-PGJ$_2$ (Biomol, Plymouth Meeting, Pennsylvania) for 24 hours. Cell lysates were prepared in RIPA buffer. Lysates were sonicated for 20 seconds on ice and centrifuged at 10,000×g for 10 minutes to sediment the particulate material. The protein concentration of the supernatant was measured by the method of Lowry, O. H., et al, J. Biol. Chem. 193, 265–275 (1951). Cellular lysate protein (100 μg/lane) was loaded onto a 10% SDS-polyacrylamide gel, electrophoresed and subsequently transferred onto nitrocellulose (Schleicher & Schuell, Keene, New Hampshire). The immunoblot was probed with antibody specific for HER-2/neu (Santa Cruz Biotechnology, Inc., Santa Cruz, Calif.). Western blotting detection reagents were purchased from Amersham Pharmacia Biotech. The immunoblot analysis showed both ciglitazone and 15-d-PGJ$_2$ decreased the amount of HER-2/neu in 184B5/HER cells.

BT474 cells were treated with vehicle (0.01% dimethyl sulfoxide) or 25 μM ciglitazone. Cell lysates were prepared and immunoblot analysis was carried out as described in the above paragraph for 184B5/HER cells. The analysis showed ciglitazone decreased amounts of HER-2/neu in BT474 cells.

Northern blotting was performed to evaluate whether PPARγ ligands decrease levels of HER-2/neu mRNA. 184B5/HER cells were treated with vehicle (0.01% dimethyl sulfoxide), 25 μM ciglitazone or 20 μM 15-d-PGJ2. Total cellular RNA was isolated from cell monolayers using an RNA isolation kit from Qiagen Inc. 10 μg of RNA was added to each lane. The 10 μg of total cellular RNA per lane were electrophoresed in a formaldehyde-containing 1.2% agarose gel and transferred to nylon-supported membranes. The blot was hybridized with probes that recognized HER-2/neu mRNA (Santa Cruz Biotechnology, Inc., Santa Cruz, Calif.) and 18S rRNA cDNA (Ambion, Inc., Austin, Tex.). Both ciglitazone and 15-d-PGJ$_2$ were found to decrease amounts of HER-2/neu mRNA.

To determine whether PPARγ ligands inhibit the transcription of HER-2/neu, a nuclear run-off assay was carried out. 184B5/HER cells were treated with vehicle (0.01% dimethyl sulfoxide) or ciglitazone (5,10 or 25 μM) for 24 hours. $2.5 \times 10^5$ cells were plated in four T150 dishes for each condition. Cells were grown in growth medium until 60% confluent. Nuclei were isolated and stored in liquid nitrogen. The HER-2/neu and 18S rRNA cDNAs were immobilized on a nitrocellulose membrane (Schleicher & Schuell, Keene, N.H.) and prehybridized overnight in hybridization buffer. The transcription assay was performed as described in Subbaramaiah, K; et al, J. Biol. Chem. 273, 21875–21882 (1998). The experiment showed that ciglitazone caused dose-dependent suppression of HER-2/neu transcription.

To determine whether PPARγ ligands inhibit HER-2/neu promoter activity, a transient transfection assay was performed. 184B5/HER cells were transfected with 1.8 μg of a human HER-21neu promoter construct ligated to luciferase (−1571/−−24) and 0.2 μg pSVβgal (Promega Corp., Madison Wis.). The HER-2/neu promoter (−1571/−−24) is described in Hudson, L. G. et al, J. Biol. Chem. 265, 4389–4393 (3/90), the whole of which is incorporated herein by reference. The promoter constructs are described in Hudson, L. G., et al, Cell 62, 1165–1175(1990). 184B5/HER cells were seeded at a density of $5 \times 10^4$ cells well in 6-well dishes and grown to 50–60% confluence. For each well, 2 μg of plasma DNA were introduced into cells using 8 μg of LIPOFECTAMINE (Life Technologies, Inc., Grand Island, N.Y.) as per the manufacturer's instructions. Following transfection, the cells were treated with ciglitazone (0, 5, 10, 15, 20 and 25 μM) or 15d-PGJ$_2$ (0, 5, 10, 15, 20 and 25 μM) for 24 hours.

The activities of luciferase and β-galactosidase were measured in cellular extract as described in Mestre, J. R. et al, Cancer Res. 57, 1081–1085 (1997). The results are shown in FIG. 1 where luciferase activity represents data that have been normalized to β-galactosidase activity (columns, means; bars, S. D.; n=6; * means $p < 0.01$ compared to control. The results show that ciglitazone and 15-d-PGJ$_2$ inhibited HER-2 neu promoter activity in a dose-dependent fashion.

BACKGROUND EXAMPLE 2

Showing that PPARγ Ligands Cause Decrease in Amount of EFGR in Human Mammary Epithelial Cells The cells used were 184B5 cells. The 184B5 cell line was obtained from a collaborator and is an immortalized but non-tumorigenic human breast epithelial cell line that was established from a reduction mammaplasty and is described in Stampler, M. R, et al, Proc. Natl. Acad. Sci. USA 82, 2394–2398 (1985).

184B5 cells were maintained in MEM-KBM mixed in a ratio of 1:1 (basal medium) containing epidermal growth factor (10 ng/ml), hydrocortisone (0.5 μg/ml), transferrin (10 μg/ml), gentamicin (5 μg/ml), and insulin (10 μg/ml) (growth medium). 184B5 cells were grown to 60% confluence, trypsinized with 0.05% trypsin-2 mM ethylene-diaminotetraacetic acid and plated for experimental use.

184B5 cells were treated with vehicle (0.01% dimethyl sulfoxide), ciglitazone (5, 10, 20, 30 μM) or 15-d-PGJ$_2$ (5, 10 μM) for 24 hours. Cell lysates were prepared in RIPA buffer. Lysates were sonicated for 20 seconds on ice and centrifuged at 10,000×g for 10 minutes to sediment the particulate material. The protein concentration of the supernatant was measured by the method of Lowry,. O. H., et al, J. Biol. Chem. 193, 265–275 (1951). Cellular lysate protein (100 μg/lane) was loaded onto a 10% SDS-polyacrylamide gel, electrophoresed and subsequently transferred onto a nitrocellulose membrane(Schleicher & Schuell Keene, N. H.). The immunoblot was probed with specific antibody for EGFR (Sigma Chemical Co., St. Louis, Miss.). Western blotting reagents were purchased from Amersham Pharmacia Biotech. The immunoblot analysis showed both ciglitazone and 15-d-$PGJ_2$ decreased amounts of EGFR in 184B5 mammary epithelial cells.

To determine whether PPARγ ligands inhibit the transcription of EGFR, a nuclear run-off assay was carried out. 184B5 cells were treated with vehicle (0.01% dimethyl sulfoxide) or ciglitazone (5, 10, 25 μM) for 24 hours. 2.5×105 cells were plated in four T150 dishes for each condition. Cells were grown in growth medium until 60% confluent. Nuclei were isolated and stored in liquid nitrogen. The EGFR and 18S rRNA cDNAs were immobilized onto a nitrocellulose membrane (Schleicher & Schuell, Keene, N.H.) and prehybridized overnight in hybridization buffer. The transcription assay was performed as described in Subbaramaiah, K, et al, J. Biol. Chem. 273, 21875–21882 (1998). The experiment showed that ciglitazone caused dose-dependent suppression of EGFR transcription.

Figure 2:
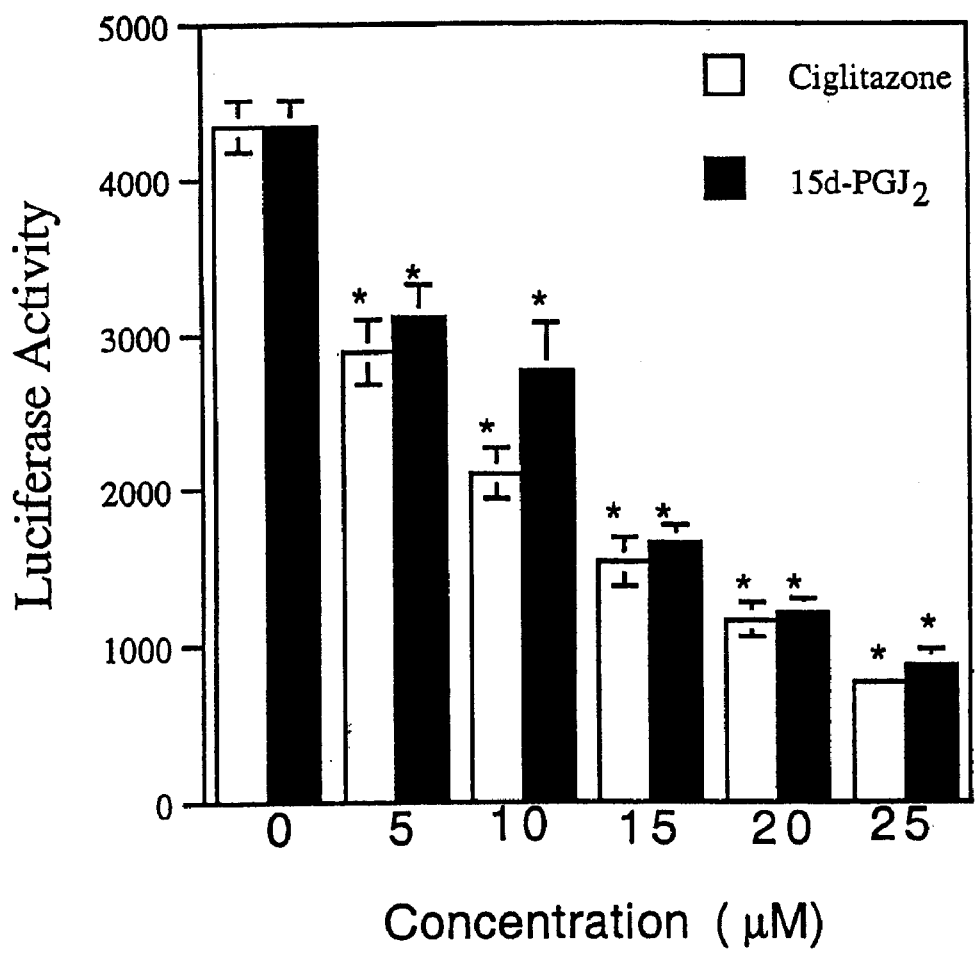
FIG. 2 is a graph of concentration of ciglitazone and 15-d-$PGJ_2$ versus luciferase activity and shows results of Background Example 2.

To determine whether PPARγ ligands inhibit EGFR promoter activity, a transient transfection assay was performed, 184B5 cells were transfected with 1.8 μg of a human EGFR promoter construct ligated luciferase (-1100/–19) and 0.2 μg pSVβgal (Promega Corp., Madison, Wis.). The EGFR promoter is described in Hudson, L. G., et al, Cell 62, 1165–1175 (1990), the whole of which is incorporated herein by reference. 184B5 cells were seeded at a density of $5×10^4$ cells/well in 6-well dishes and grown to 50–60% confluence. For each well 2 μg of plasma DNA were introduced into cells using 8 μg of LIPOFECTAMINE (Life Technologies, Inc., Grand Island, N.Y.) as per the manufacturers instructions. Following transfection, the cells were treated with ciglitazone (0, 5, 10, 15, 20 and 25 μM) or 15-d-$PGJ_2$ (0, 5, 10, 15, 20, and 25 μM) for 24 hours. The activities of luciferase and β-galactosidase were measured in cellular extract as described in Mestre, J. R, et al, Cancer Res. 57, 1081–1085 (1997). The results are shown in FIG. 2 where luciferase activity represents data that have been normalized to β-galactosidase activity (columns, means; bars, S. D., n=6; * means p<0.01 compared to control). The results show that ciglitazone and 15-d-$PGJ_2$ inhibited EGFR promoter activity in a dose-dependent fashion.

EXAMPLE I

A patient with HER-2/neu positive breast cancer is treated with ciglitazone or troglitazone or pioglitazone or rosiglitazone for adjuvant therapy at an oral dose of 5 mg/kg twice per day for five years after a mastectomy. Recurrence of breast cancer does not occur.

When GW 7845 or the compound of structure (II) or (III) is given at an oral dose of 5 mg/kg twice per day for five years after a mastectomy in place of the thiazolidinedione, recurrence of breast cancer does not occur.

EXAMPLE II

A patient with HER-2/neu positive breast cancer is treated with PPARγ ligand and HERCEPTIN® for adjuvant therapy. The patient received a loading dose of 250 mg intravenous HERCEPTIN®, then 10 weekly doses of 125 mg each IV. The patient also received an oral dose of 5 mg/kg ciglitazone or troglitazone or pioglitazone or rosiglitazone twice daily for one year or 5 mg/kg of GW 7845 or compound of structure (II) or (III) twice daily for one year. Recurrence of breast cancer does not occur.

EXAMPLE III

Breast cancer is determined to have metastasized to lung and liver three years after a mastectomy is performed on a patient with HER-2/neu positive breast cancer. The patient is treated with oral doses of 5 mg/kg of ciglitazone or troglitazone or pioglitazone or rosiglitazone twice daily or 5 mg/kg of GW 7845 or compound of structure (II) or (III) twice daily. A reduced tumor burden is noted.

After three months, the PPARγ ligand administration is continued in combination regimen with Taxol® at a dose of 175 $mg/m^2$ administered intravenously every three weeks. A further reduced tumor burden is noted.

EXAMPLE IV

Breast cancer is determined to have metastasized to bone nine years after a mastectomy is performed on a patient with HER-2/neu positive breast cancer.

After failure of prior chemotherapy regimens, the patient is treated with an oral dose of 5 mg/kg of ciglitazone or troglitazone or pioglitazone or rosiglitazone twice daily or 5 mg/kg of GW 7845 or compound of structure (II) or (III) twice daily and HERCEPTIN® at a loading dose of 250 mg IV followed by 10 weekly doses of 125 mg each IV. A reduced tumor burden is noted.

After 90 days, oral cyclophosphamide at a dose of 3 mg/kg/day and doxorubicin administered intravenously weekly at a dose of 20 $mg/m^2$, are added to the drug regimen. A still further reduced tumor burden is noted.

EXAMPLE V

A patient undergoes resection of colon cancer which proves to be HER-2/neu positive. The colon cancer is found to be localized to the bowel wall; there is no evidence of extracolonic cancer. The patient is treated with an oral dose of 5 mg/kg of ciglitazone or troglitazone or pioglitazone or rosiglitazone twice daily or 5 mg/kg of GW 7845 or compound of the structure (II) or (III) twice daily, for five years. Recurrence of colon cancer does not occur.

EXAMPLE VI

A patient with non-small cell lung carcinoma metastasized to liver, where EGFR is determined to be overexpressed, is treated with oral doses of 5 mg/kg of ciglitazone or troglitazone or pioglitazone or rosiglitazone twice daily or 5 mg/kg of GW 7845 or compound of structure (II) or (III) twice daily. A reduced tumor burden is noted. After one month, PPARγ ligand administration is continued in combination with infusion of cisplatin every four weeks at 60 $mg/m^2$ for 12 more weeks. A further reduced tumor burden is noted.

EXAMPLE VII

A patient with head and neck carcinoma where EGFR is overexpressed is treated intravenously with a loading dose of 400 $mg/m^2$ of CETUXIMAB® followed by weekly infusions of 300 $mg/m^2$ of CETUXIMAB® for 12 weeks.

Concurrently cisplatin is infused every four weeks at 60 mg/m². A reduced tumor burden is noted. At the end of the 12 week period, treatment is started with 5 mg/kg twice daily by oral administration of ciglitazone or troglitazone or pioglitazone or rosiglitazone or GW 7845 or compound of structure (II) or (E) for 12 weeks. A further reduced tumor burden is noted.

EXAMPLE VIII

A patient with breast cancer with Stage IV EGFR positive tumors is treated with a loading dose of CETUXIMAB® of 400 mg/m² followed by weekly infusions of 300 mg/m² of CETUXIMAB® in combination regimen with Taxol® at a dose of 175 mg/m² administration intravenously every three weeks in further combination regimen with oral doses twice daily of 5 mg/kg of ciglitazone or troglitazone or pioglitazone or rosiglitazone or GW 7845 or compound of structure (I) or (III). A reduced tumor burden is noted.

EXAMPLE IX

A patient with EGFR positive breast cancer is treated with ciglitazone or troglitazone or pioglitazone or rosiglitazone or GW 7845 or compound of structure (II) or (III) at an oral dose of 5 mg/kg twice per daily for five years after a mastectomy. Recurrence of breast cancer dose not occur.
Variations Many variations of the above will be obvious to those skilled in the art. Thus, the invention is defined by the claims.

What is claimed is:

1. A method for downregulating expression of at least one member of the class I family of receptor tyrosine kinases selected from the group consisting of HER-2/neu and epidermal growth factor receptor in a patient affected with cancer associated with overexpression of at least one member of the class I family of receptor tyrosine kinases selected from the group consisting of HER-2/neu and epidermal growth factor rector, comprising administering to said patient a therapeutically effective amount of a ligand of peroxisome proliferator-activated receptor gamma (PPARγ) which has a $pK_i$ of at least 4.0 in binding assay using human PPARγ binding domain.

2. The method of claim 1 where the cancer is associated with overexpression of HER-2/neu and the patient is one to whom anti-HER-2/neu antibody is also administered in a therapeutically effective amount.

3. The method of claim 1 where the cancer is associated with the overexpression of epidermal growth factor receptor and the patient is one to whom anti-epidermal growth factor receptor is also administered in a therapeutically effective amount.

4. The method of claim 1 where the ligand of PPARγ is a thiazolidinedione.

5. The method of claim 4 where the thiazolidinedione is ciglitazone.

6. The method of claim 4 where the thiazolidinedione is selected from the group consisting of troglitazone, pioglitazone and rosiglitazone.

7. The method of claim 1 where the ligand of PPARγ is (S)-2-(1-carboxy-2-{4-[2-(5-methyl-2-phenyloxazol-4-yl)ethoxy]phenyl}ethylamino)benzoic acid methyl ester.

8. The method of claim 1 where the ligand of PPARγ is 3-{4-[2-benzoxazol-2-ylmethylamino)ethoxy]phenyl}-(2S)-((2-benzoylphenyl)amino)propionic acid.

9. The method of claim 1 where the ligand of PPARγ is (2S)-((2-benzoylphenyl)amino)-3-{4-[2-(5-methyl-2-phenyloxazol-4-yl)ethoxy]phenyl}-propionic acid.

10. The method of claim 1 where the ligand of PPARγ is administered in combination regime with other therapy for the cancer.

11. The method of claim 1 where the cancer is HER-2/neu positive breast cancer.

12. The method of claim 11 where the ligand of PPARγ is administered for or as part of adjuvant therapy.

13. The method of claim 12 where the PPARγ ligand is a thiazolidinedione.

14. The method of claim 13 where the thiazolidinedione is ciglitazone.

15. The method of claim 13 where the thiazolidinedione is selected from the group consisting of troglitazone, pioglitazone and rosiglitazone.

16. The method of claim 12 where the ligand of PPARγ is (S)-2-(1-carboxy-2-{4-[2-(5-methyl-2-phenyloxazol-4-yl)ethoxy]phenyl}ethylamino)benzoic acid methyl ester.

17. The method of claim 12 where the ligand of PPARγ is 3-{4-[2-benzoxazol-2-ylmethylamino)ethoxy]phenyl}-(2S)-((2-benzoylphenyl)amino)propionic acid.

18. The method of claim 12 where the ligand of PPARγ is (2S)-((2-benzoylphenyl)amino 3-{4-[2-(5-methyl-2-phenyloxazol-4-yl)ethoxy]phenyl}-propionic acid.

19. The method of claim 11 where the cancer is HER-2/neu positive breast cancer that has metastasized.

20. The method of claim 19 where the ligand of PPARγ is administered in combination regimen with a therapeutically effective amount of anti-HER-2/neu antibody.

21. The method of claim 20 where the ligand of PPARγ and anti-HER-2/neu antibody are administered in combination regimen with standard therapy for metastasized breast cancer.

22. The method of claim 19 wherein the ligand of PPARγ is administered in combination regimen with standard therapy for metastasized breast cancer.

23. The method of claim 19 where the PPARγ ligand is a thiazolidinedione.

24. The method of claim 23 where the thiazolidinedione is ciglitazone.

25. The method of claim 23 wherein the thiazolidinedione is selected from the group consisting of troglitazone, pioglitazone and rosiglitazone.

26. The method of claim 19 wherein the ligand of PPARγ is (S)-2-(1-carboxy-2-{4-[2-(5-methyl-2-phenyloxazol-4-yl)ethoxy]phenyl}ethylamino)benzoic acid methyl ester.

27. The method of claim 19 wherein the ligand of PPARγ is 3-{4-[2-benzoxazol-2-ylmethylamino)ethoxy]phenyl}-(2S)-((2-benzoylphenyl)amino)propionic acid.

28. The method of claim 19 wherein the ligand of PPARγ is (2S)-((2-benzoylphenyl)amino)-3-{4-[2-(5-methyl-2-phenyloxazol-4-yl)ethoxy]phenyl}-propionic acid.

* * * * *

UNITED STATES PATENT AND TRADEMARK OFFICE
CERTIFICATE OF CORRECTION

PATENT NO.   : 6,291,496 B1  
DATED        : September 18, 2001  
INVENTOR(S)  : Andrew J. Dannenberg and Kotha Subbaramaiah Page 1 of 1

It is certified that error appears in the above-identified patent and that said Letters Patent is hereby corrected as shown below:

Title page,
Change "[76]" to -- [75] --.
Add -- [73] Assignee: Cornell Research Foundation, Inc., Ithaca, New York (US) --.

Column 13, claim 1,
Line 39, change "rector" to -- receptor --.

Column 14, claim 18,
Line 29, after "amino", insert -- )- --.

Signed and Sealed this

Sixteenth Day of April, 2002

Attest:

Attesting Officer

JAMES E. ROGAN
*Director of the United States Patent and Trademark Office*